(12) United States Patent
Hyeon

(10) Patent No.: US 11,278,263 B2
(45) Date of Patent: Mar. 22, 2022

(54) ULTRASOUND APPARATUS AND METHOD OF CONTROLLING THE SAME

(71) Applicant: SAMSUNG MEDISON CO., LTD., Gangwon-do (KR)

(72) Inventor: Yong Cheol Hyeon, Seoul (KR)

(73) Assignee: SAMSUNG MEDISON CO. LTD., Ganwon-Do (KR)

( * ) Notice: Subject to any disclaimer, the term of this patent is extended or adjusted under 35 U.S.C. 154(b) by 113 days.

(21) Appl. No.: 16/783,527

(22) Filed: Feb. 6, 2020

(65) Prior Publication Data

US 2020/0261064 A1 Aug. 20, 2020

(30) Foreign Application Priority Data

Feb. 15, 2019 (KR) ........................ 10-2019-0018016

(51) Int. Cl.
*A61B 8/00* (2006.01)

(52) U.S. Cl.
CPC ............ *A61B 8/546* (2013.01); *A61B 8/4477* (2013.01); *A61B 8/46* (2013.01); *A61B 8/56* (2013.01); *A61B 8/58* (2013.01)

(58) Field of Classification Search
CPC ......... A61B 8/546; A61B 8/4477; A61B 8/46; A61B 8/56; A61B 8/58; G01S 7/52074;
(Continued)

(56) References Cited

U.S. PATENT DOCUMENTS

2009/0028211 A1  1/2009  Amemiya
2009/0054783 A1  2/2009  Shibata
(Continued)

FOREIGN PATENT DOCUMENTS

| JP | 4510476 B2 | 7/2010 |
| JP | 2016-137011 A | 8/2016 |
| KR | 10-2017-0065401 A | 6/2017 |

OTHER PUBLICATIONS

Extended European Search Report dated Aug. 5, 2020 issued in European Patent Application No. 20157420.9.

*Primary Examiner* — Joseph M Santos Rodriguez
(74) *Attorney, Agent, or Firm* — Morgan, Lewis & Bockius LLP

(57) ABSTRACT

An ultrasound apparatus includes a plurality of channels, each including a transmission channel for generating and outputting a transmission signal based on a synchronization signal, a temperature detector for outputting a temperature information signal of the transmission channel, a transducer element for converting the transmission signal output from the transmission channel into an ultrasound signal and outputting the ultrasound signal, a reception channel for receiving a reception signal that returns after the ultrasound signal is transmitted to and reflected from an object, and acquiring ultrasound image data based on the received reception signal, and a switching circuit for connecting the temperature detector to the reception channel such that the reception channel receives the temperature information signal of the transmission channel. The reception channel generates a control signal for closing or opening the switching circuit, and the switching circuit is closed or opened on the generated control signal.

16 Claims, 14 Drawing Sheets

(58) Field of Classification Search
CPC . G01S 7/52073; G01S 7/5205; G01S 15/8925
See application file for complete search history.

(56) References Cited

U.S. PATENT DOCUMENTS

| | | |
|---|---|---|
| 2012/0226160 A1 | 9/2012 | Kudoh |
| 2014/0005546 A1* | 1/2014 | Haider .................. A61B 8/546 |
| | | 600/447 |
| 2015/0150502 A1 | 6/2015 | Wu |
| 2015/0164483 A1 | 6/2015 | Miyajima et al. |

* cited by examiner

ULTRASOUND APPARATUS AND METHOD OF CONTROLLING THE SAME

CROSS-REFERENCE TO RELATED APPLICATION

This application is based on and claims priority under 35 U.S.C. § 119 to Korean Patent Application No. 2019-0018016, filed on Feb. 15, 2019 in the Korean Intellectual Property Office, the disclosure of which is incorporated herein by reference.

BACKGROUND

1. Field

The present disclosure relates to an ultrasound apparatus for determining whether the ultrasound apparatus is normally operated by individually detecting temperature information of a plurality of transmitters of the ultrasound apparatus or waveforms of generated transmission signals, and a method of controlling the same.

2. Description of the Related Art

Ultrasound apparatuses operate to irradiate an ultrasound signal generated from an ultrasound probe transducer to a target site inside an object through the surface of the object and receive an ultrasound signal (ultrasound echo signal) reflected from the object to acquire an image of the internal state of the object.

The ultrasound diagnosis apparatus has advantages in that it is compact and inexpensive, is displayable in real time, and has high safety compared to X-ray diagnostic devices due to having no risk of exposure to X-rays or the like, and thus are widely used in a variety of fields, such as medical fields and the like.

The ultrasound imaging apparatus includes a plurality of transmission circuits, and when one of the plurality of transmission circuit has an error, transmission circuits adjacent to the erroneous transmission circuit is caused to be broken due to the characteristic of using a high voltage power source.

In order to alleviate such a constraint, there has been a need for a circuit that may detect which transmission circuit is erroneous among a plurality of transmission circuits, but when temperature information signals of the respective transmission circuits are individually monitored, the configuration of the detection circuit becomes significantly complicated.

SUMMARY

Therefore, it is an object of the disclosure to provide an ultrasound apparatus for individually detecting temperature information of a plurality of transmission circuits using a simple circuit configuration, and a method of controlling the same.

Additional aspects of the disclosure will be set forth in part in the description which follows and, in part, will be obvious from the description, or may be learned by practice of the disclosure.

Therefore, it is an aspect of the disclosure to provide an ultrasound apparatus including a plurality of channels, each including: a transmission channel configured to generate and output a transmission signal on the basis of a synchronization signal; a temperature detector configure to output a temperature information signal of the transmission channel; a transducer element configured to convert the transmission signal output from the transmission channel into an ultrasound signal and output the ultrasound signal; a reception channel configured to receive a reception signal that returns after the ultrasound signal is transmitted to an object and is reflected from the object, and acquire ultrasound image data on the basis of the received reception signal; and a switching circuit configured to connect the temperature detector to the reception channel such that the reception channel receives the temperature information signal of the transmission channel, wherein the reception channel generates a control signal for closing or opening the switching circuit; and the switching circuit is closed or opened on the generated control signal.

The reception channel may generate the control signal for closing the switching circuit in a section other than a first section such that the temperature information signal of the transmission channel is transmitted to the reception channel; and the first section is a section in which the synchronization signal and the transmission signal are output.

The reception channel may generate the control signal for closing the switching circuit in a section other than a second section such that the output temperature information signal is transmitted to the reception channel; and the second section is a section in which the reception channel acquires the ultrasound image data on the basis of the reception signal.

The reception channel may generate the control signal for opening the switching circuit in the first section such that the output temperature information signal is prevented from being transmitted to the reception channel.

The reception channel may generate the control signal for opening the switching circuit in the second section such that the output temperature information signal is prevented from being transmitted to the reception channel.

The ultrasound apparatus may further include a controller configured to control an operation of the transmission channel, wherein the controller may determine whether a temperature of the transmission channel is higher than or equal to a reference temperature on the basis of the temperature information signal received by the reception channel, and in response to the temperature of the transmission channel being higher than or equal to the reference temperature, stops operating the transmission channel.

The plurality of channels may include a first channel and a second channel including a transducer element adjacent to a transducer element of the first channel, wherein the controller, in response to a temperature of the transmission channel included in the first channel being higher than or equal to the reference temperature, may stop operating the transmission channel included in the first channel, and control the reception channel of the first channel such that the reception channel of the first channel acquires the ultrasound image data on the basis of a reception signal received by the reception channel of the second channel.

The ultrasound apparatus may further include a display, wherein the controller, in response to the temperature of the transmission channel being higher than or equal to the reference temperature, may allow the display to indicate that an error exists in the ultrasound apparatus.

The ultrasound apparatus may further include a display, wherein the controller, in response to the temperature of the transmission channel being higher than or equal to the reference temperature, may allow the display to indicate that an error exists in the channel including the transmission channel.

The reception channel may generate the control signal having a predetermined period, and the predetermined period may be a value obtained by multiplying a period of the synchronization signal by a positive integer.

It is another aspect of the disclosure to provide a method of controlling an ultrasound apparatus including a plurality of channels each including a transmission channel, a temperature detector, a transducer element, a reception channel, and a switching circuit configured to connect the temperature detector and the reception channel, the method including: generating and outputting a transmission signal on the basis of a synchronization signal; converting the output transmission signal into an ultrasound signal and output the ultrasound signal; receiving a reception signal that returns after the ultrasound signal is transmitted to an object and is reflected from the object, and acquiring ultrasound image data on the basis of the received reception signal; outputting a temperature information signal of the transmission channel; and generating a control signal for closing or opening the switching circuit such that the reception channel receives the output temperature information signal of the transmission channel, The generating of the control signal for closing or opening the switching circuit may include generating the control signal for closing the switching circuit in a section other than a first section such that the temperature information signal of the transmission channel is transmitted to the reception channel, wherein the first section may be a section in which the synchronization signal and the transmission signal are output.

The method may further include generating the control signal for closing the switching circuit in a section other than a second section such that the temperature information signal of the transmission channel is transmitted to the reception channel, wherein the second section may be a section in which the reception channel acquires the ultrasound image data on the basis of the reception signal.

The method may further include generating the control signal for opening the switching circuit in the first section such that the output temperature information signal is prevented from being transmitted to the reception channel.

The method may further include generating the control signal for opening the switching circuit in the second section such that the output temperature information signal is prevented from being transmitted to the reception channel.

The method may further include determining whether a temperature of the transmission channel is higher than or equal to a reference temperature on the basis of the temperature information signal received by the reception channel, and in response to the temperature of the transmission channel being higher than or equal to the reference temperature, stopping the operation of the transmission channel.

The plurality of channels may include a first channel and a second channel including a transducer element adjacent to a transducer element of the first channel, wherein the method may further include, in response to a temperature of the transmission channel included in the first channel being higher than or equal to the reference temperature, stopping the operation of the transmission channel included in the first channel, and controlling the reception channel of the first channel such that the reception channel of the first channel acquires the ultrasound image data on the basis of a reception signal received by the reception channel of the second channel.

The method may further include: in response to the temperature of the transmission channel being higher than or equal to the reference temperature, indicating an error exists in the ultrasound apparatus.

The method may further include: in response to the temperature of the transmission channel being higher than or equal to the reference temperature, indicating an error exists in the channel including the transmission channel.

The generating of the control signal for closing or opening the switching circuit may include generating the control signal having a predetermined period, and the predetermined period may be a value obtained by multiplying a period of the synchronization signal by a positive integer.

BRIEF DESCRIPTION OF THE DRAWINGS

These and/or other aspects of the disclosure will become apparent and more readily appreciated from the following description of the embodiments, taken in conjunction with the accompanying drawings of which.

DETAILED DESCRIPTION

Figure 1:
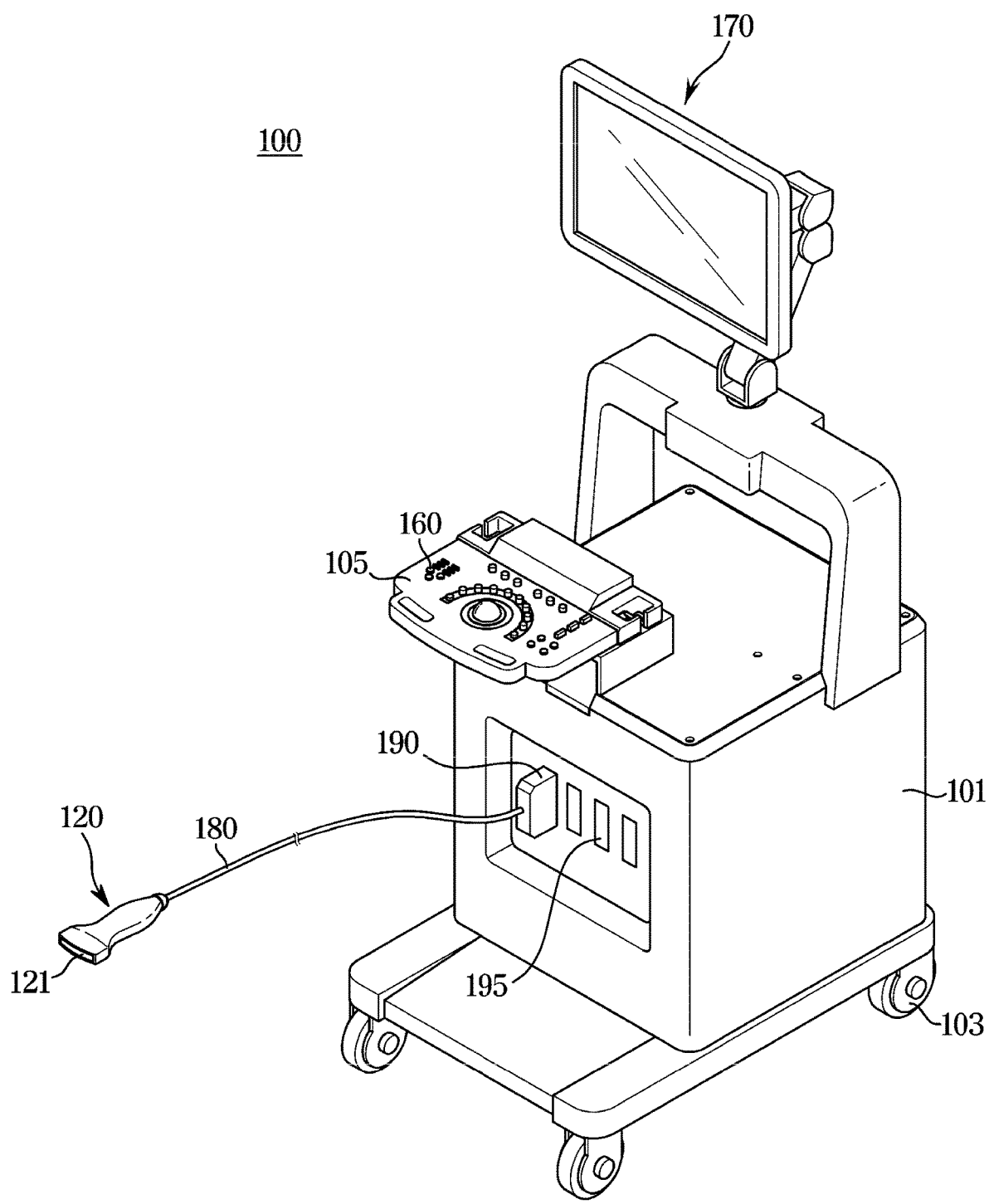
FIG. 1 is an external view illustrating an ultrasound apparatus according to an embodiment.

Like numerals refer to like elements throughout the specification. Not all elements of embodiments of the present disclosure will be described, and description of what are commonly known in the art or what overlap each other in the embodiments will be omitted. The terms as used throughout the specification, such as "~part", "~module", "~member", "~block", etc., may be implemented in software and/or hardware, and a plurality of "~parts", "~modules", "~members", or "~blocks" may be implemented in a single element, or a single "~part", "~module", "~member", or "~block" may include a plurality of elements.

It will be further understood that the term "connect" or its derivatives refer both to direct and indirect connection, and the indirect connection includes a connection over a wireless communication network.

It will be further understood that the terms "comprises" and/or "comprising," when used in this specification, specify the presence of stated features, integers, steps, operations, elements, and/or components, but do not preclude the presence or addition of one or more other features, integers, steps, operations, elements, Further, it will be further understood when a signal or data is transferred, sent or transmitted from "an element" to "another element", it does not exclude another element between the element and the other element passed by the signal or data therethrough, unless the context clearly indicates otherwise.

Although the terms "first," "second," "A," "B," etc. may be used to describe various components, the terms do not limit the corresponding components, but are used only for the purpose of distinguishing one component from another component.

As used herein, the singular forms "a," "an" and "the" are intended to include the plural forms as well, unless the context clearly indicates otherwise.

Reference numerals used for method steps are just used for convenience of explanation, but not to limit an order of the steps. Thus, unless the context clearly dictates otherwise, the written order may be practiced otherwise.

Hereinafter, embodiments of an ultrasound apparatus 100 according to an aspect and a method of controlling the same will be described with reference to the accompanying drawings in detail.

FIG. 1 is an external view illustrating an ultrasound apparatus according to an embodiment.

Referring to FIG. 1, the ultrasound apparatus 100 according to the embodiment includes an ultrasound probe 120 including a plurality of transducer elements 121 for transmitting an ultrasound signal to an object, receiving an ultrasound echo signal reflected from the object, and converts the received ultrasound echo signal into an electrical signal, a main body 101, an input 160, and a display 170.

The ultrasound probe 120 may be connected to the main body 101 through a cable 180 to receive various signals required for controlling the ultrasound probe 120 or transmit a reception signal corresponding to the ultrasound echo signals received by the ultrasound probe 120.

The reception signal may be one of an analogue signal and a digital signal into which the ultrasound echo signal has been electrically converted by the ultrasound probe 120.

The main body 101 may be provided at one side thereof with one or more female connectors 195. A male connector 190 provided at one end of the cable 180 may be physically coupled to the female connector 195.

However, the embodiment of the ultrasound probe 120 is not limited thereto, and the ultrasound probe 120 may be wirelessly connected to the main body 101. In this case, the ultrasound probe 120 may be implemented as a wireless probe to transmit and receive signals through a network formed between the ultrasound probe 120 and the main body 101. In addition, a plurality of the ultrasound probes 120 may be connected to a single main body 101.

The plurality of transducer elements 121 included in the ultrasound probe 120 may form a transducer array, and the transducer array may be a two-dimensional array as described below in FIG. 10.

The main body 101 is provided at a lower portion with a plurality of casters 103 for the movement of the ultrasound apparatus 100. The user may fix or move the ultrasound apparatus 100 using the plurality of casters 103. Such an ultrasound apparatus 100 is referred to as a cart-type ultrasound apparatus 100.

The main body 101 is provided at a front surface with an operation panel 105. The input 160 for receiving a user's input may be formed on the operation panel 105, and allows a user to input commands for starting a diagnosis, selecting a diagnosis site, selecting a diagnosis type, selecting a mode for ultrasound image through the input 160.

The display 170 may be provided at an upper side of the main body 101. The display 170 may be implemented as at least one of various display panels, such as a liquid crystal display (LCD) panel, a light emitting diode (LED) panel, or an organic light emitting diode (OLED) panel.

In addition, the display 170 may be composed of two or more displays such that each display simultaneously displays a different image. For example, one display may display a 2D ultrasound image, and the other display may display a 3D ultrasound image. Alternatively, one display may display a B-mode image, and the other display may display a contrast agent image. Alternatively, one display may display an ultrasound image, and the other display may display a temperature information signal of a transmission channel.

In addition, the display 170 may display an ultrasound image on the basis of the reception signal received from the ultrasound probe 120.

In addition, the display 170, in response to an error found in a transmission channel of the ultrasound apparatus 100, may display a phrase or a figure informing the user that the ultrasound apparatus 100 or a channel including the transmission channel has an error.

A user, such as a doctor, may diagnose a specific disease using the ultrasound image displayed on the display 170, and the site for acquiring the ultrasound image may vary according to a diagnosis target disease.

In addition, a user, such as a doctor, may determine whether the ultrasound apparatus 100 is normally operated on the basis of the phrase or figure, indicating that the ultrasound apparatus 100 or the transmission channel has an error, displayed on the display 170. With such a configuration, the patient may be protected from abnormal operation during use of the ultrasound apparatus 100 and the probability of misdiagnosis may be reduced.

One or more probe holders for mounting the ultrasound probe 120 may be provided on an outer circumferential surface of the main body 101. Accordingly, when the user does not use the ultrasound probe 120, the user may store the ultrasound probe 120 on the probe holder.

The main body 101 includes a transmitter 210 including a plurality of transmission channels 210-1, 210-2, . . . , and 210-N and a plurality of pulsers, a plurality of switching circuits 240-1, 240-2, . . . and 240-N each connected to a corresponding one of the plurality of pulsers, a receiver 220 including a plurality of reception channels 220-1, 220-2, . . . and 220-N, an image processor 161, and a controller 150. The transmitter 210, the plurality of switching circuits 240-1, 240-2, . . . , and 240-N, the receiver 220, the image processor 161, and the controller 150 may include at least one memory in which a program for performing operations of the ultrasound apparatus 100 is stored and at least one processor for executing the stored program.

The transmitter 210, the plurality of switching circuits 240-1, 240-2, . . . , and 240-N, the receiver 220, the image processor 161, and the controller 150 may use separate memories and separate processors, or may share a memory and a processor.

On the other hand, the appearance of the ultrasound apparatus 100 according to the embodiment is not limited to the example shown in FIG. 1. For example, the ultrasound apparatus 100 may be implemented in a portable type. When the ultrasound apparatus 100 is implemented as a portable type, the main body 101 may be provided in the form of a laptop computer, a personal digital assistant (PDA), a tablet personal computer (PC), and the like, and when connected to the ultrasound probe 120, may generates an ultrasound image.

Figure 2:
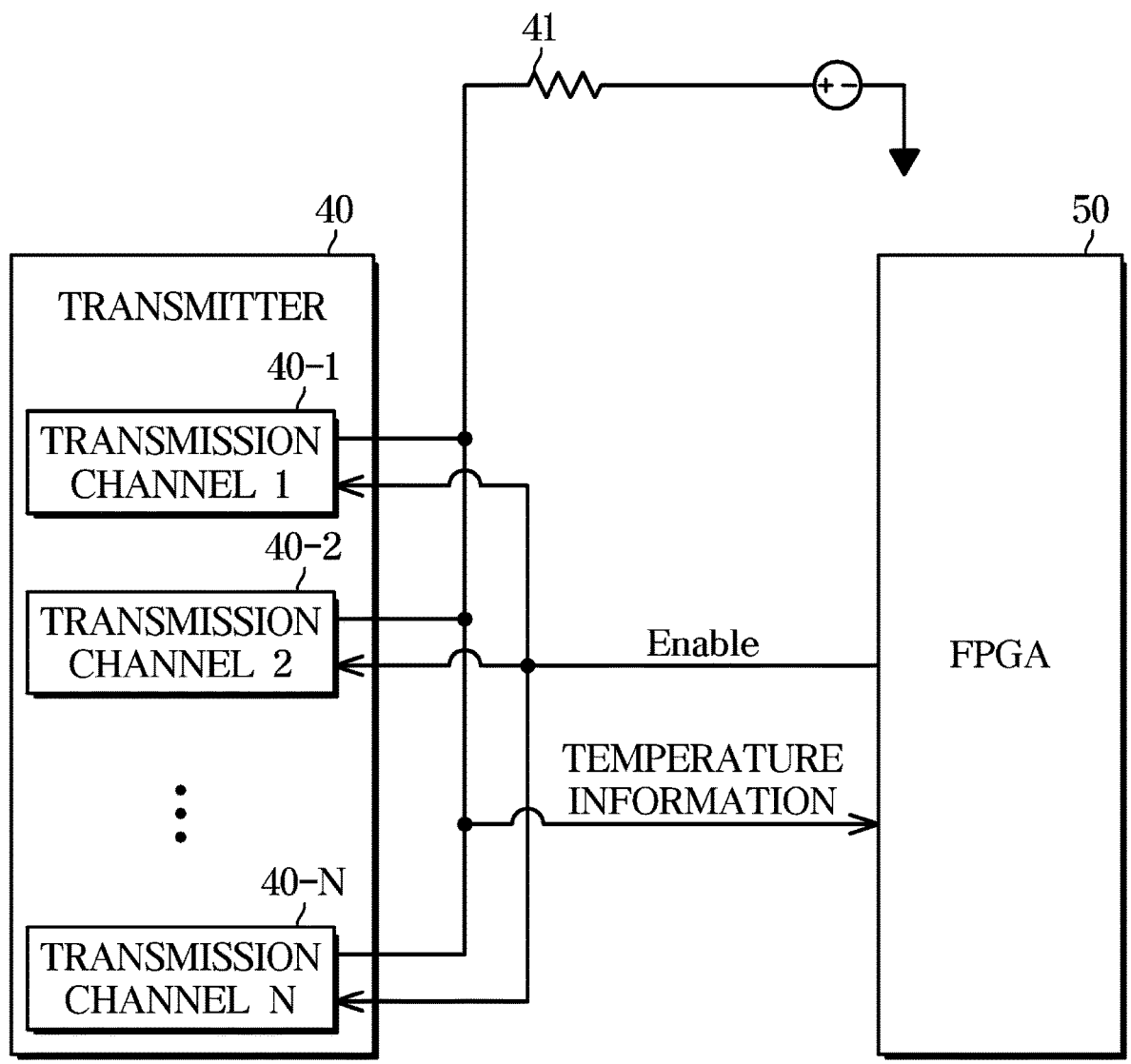
FIG. 2 is a block diagram illustrating a conventional ultrasound apparatus for collectively detecting pieces of temperature information of transmitting circuits.

FIG. 2 is a block diagram illustrating a conventional ultrasound apparatus for collectively detecting pieces of temperature information of transmitting circuits.

Referring to FIG. 2, a transmitter 40 of a conventional ultrasound apparatus includes a plurality of transmission channels 40-1, 40-2, . . . , and 40-N.

A field programmable gate array (FPGA) 50 is configured to detect temperature information of the plurality of transmission channels 40-1, 40-2, . . . and 40-N by transmitting an enable signal to each of the plurality of transmission channels 40-1, 40-2, . . . and 40-N, and temperature information signals outputted from the plurality of transmission channels 40-1, 40-2, and 40-N are combined to one signal that is then transmitted to the FPGA 50. In this case, the temperature information signal is only a digital type thermal warning signal, rather than a signal including pieces of temperature information of the plurality of transmission channels 40-1, 40-2, . . . and 40-N.

The temperature information signal is a signal in the form of a voltage, and may be transmitted to the FPGA 50 as a signal in the form of a current through a resistor element 41.

The FPGA 50 may determine, in response to receiving the temperature information signal, that an error exists in the transmitter 40 on the basis of the temperature information signal.

According to the conventional ultrasound apparatus, the temperature information signal may be transmitted only as a digital type thermal warning signal that identifies only the existence of an error in the transmitter 40 rather than identifying which one of the transmission channels 40-1, 40-2, . . . and 40-N has the error.

Therefore, even when only one of the transmission channels 40-1, 40-2 . . . and 40-N fails, the operation of the transmitter 40, that is, the operation of the ultrasound apparatus, needs to be stopped to prevent a series of breakage of other transmission channels. In addition, the user may not use the ultrasound apparatus until the ultrasound apparatus is repaired.

In addition, even when a dark line defect of an ultrasound image occurs due to a failure of one of the transmission channels 40-1, 40-2 . . . and 40-N, the faulty one of the transmission channel 40-1, 40-2 . . . and 40-N is not identified, and thus the ultrasound image is not correctable using reception signals of other channels.

Figure 3:
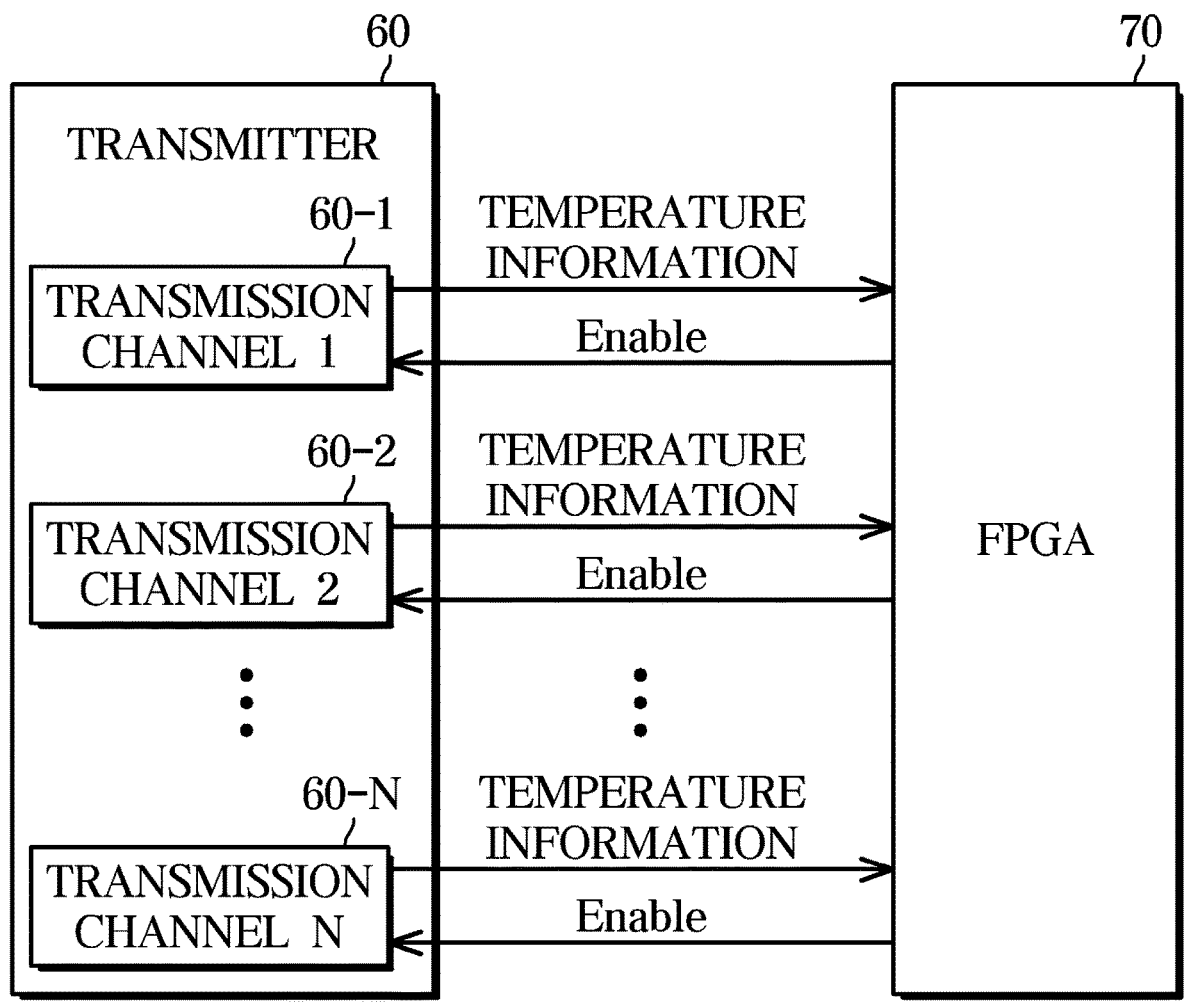
FIG. 3 is a block diagram illustrating a conventional ultrasound apparatus for individually detecting pieces of temperature information of transmitting circuits.

FIG. 3 is a block diagram illustrating a conventional ultrasound apparatus for individually detecting pieces of temperature information of transmitting circuits.

Referring to FIG. 3, an FPGA 70 is configured to detect temperature information of a plurality of transmission channels 60-1, 60-2 . . . and 60-N by transmitting an enable signal to each of the plurality of transmission channels 60-1, 60-2 . . . and 60-N, and the plurality of transmission channels 60-1, 60-2, and 60-N transmit digital type temperature information signals to the FPGA 70.

According to the conventional ultrasound apparatus described with reference to FIG. 3, unlike the conventional ultrasound apparatus described with reference to FIG. 2, the temperature information signal of each of the plurality of transmission channels 60-1, 60-2, and 60-*n* is individually transmitted to the FPGA 70, so that a specific one of the transmission channel 60-1, 60-2 . . . and 60-N that has an error may be identified, and thus only a channel including the erroneous one of the transmission channels 60-1, 60-2 . . . and 60-N is stopped.

However, since the conventional technology still transmits the temperature information signal only in the form of digital type information, and requires input circuits and output circuits between the plurality of transmission channels 60-1, 60-2 . . . and 60-N and the FPGA 70 as many as the number of channels N, the circuit configuration is complicated and costly, and thus are hardly available for the user.

In addition, referring to FIGS. 2 to 3, when the plurality of temperature information signals are transmitted as analog signals, an analog-digital converter (ADC) is required for each channel, and thus the circuit configuration becomes more complicated.

Hereinafter, referring to FIGS. 4 and 5, a channel configuration of the ultrasound apparatus 100 according to the embodiment of the present disclosure that may alleviate the limitations of the conventional technology described above with reference to FIGS. 2 to 3 will be described.

Figure 4:
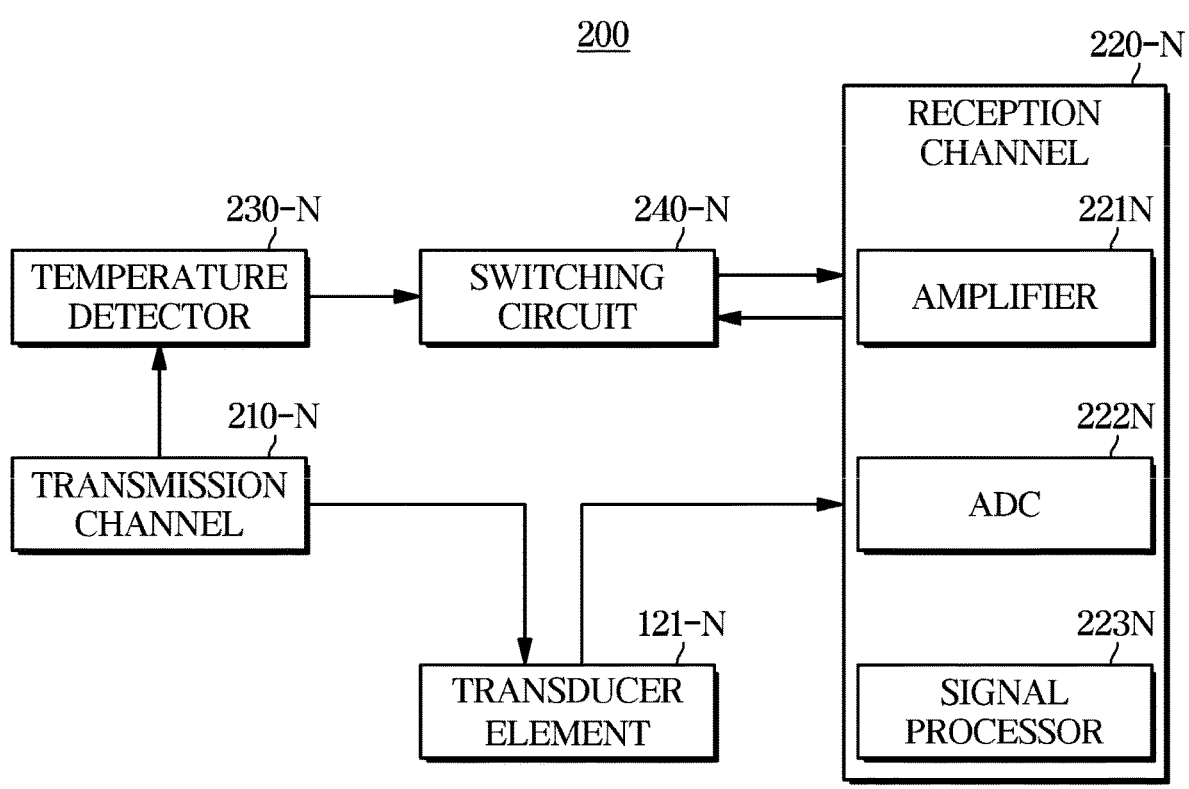
FIG. 4 is a block diagram illustrating a channel of an ultrasound apparatus according to an embodiment.
Figure 5:
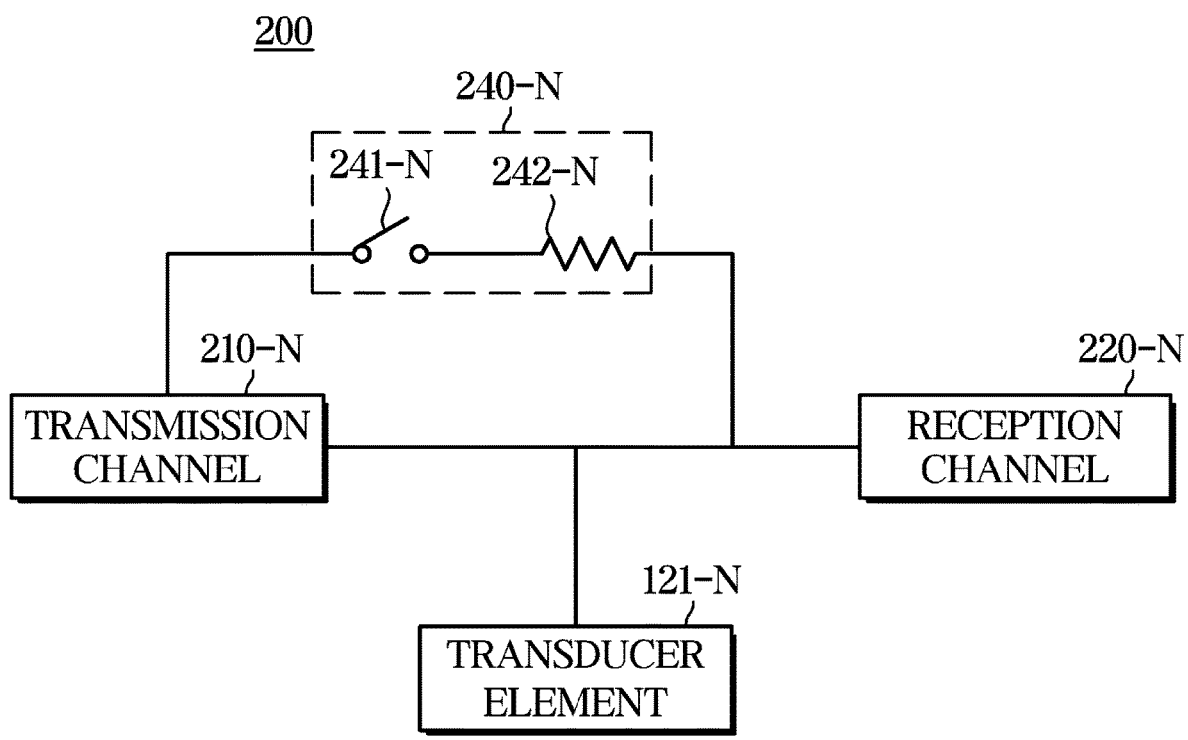
FIG. 5 is a circuit diagram illustrating a channel of an ultrasound apparatus according to an embodiment.

FIG. 4 is a block diagram illustrating the channel of the ultrasound apparatus according to the embodiment, and FIG. 5 is the circuit diagram embodiment.

All components shown In FIGS. 4 to 5 other than a switching circuit are components included in a single channel 200 of the ultrasound apparatus. For the sake of convenience in description, the following description will be made in relation to a configuration of an N-th channel (N is a natural number greater than or equal to 2) under the assumption that the ultrasound apparatus includes N channels.

The channel of the ultrasound apparatus may include a transmission channel 210-N that generates and outputs a transmission signal on the basis of a synchronization signal, a temperature detector 230-N that detects the temperature of the transmission channel 210-N and outputs a temperature information signal, and a transducer element 121-N that converts the transmission signal output from the transmitter into an ultrasound signal, transmits the ultrasound signal to an object, receives an echo signal reflected from the object, and outputs a reception signal on the basis of the echo signal, and may further include a reception channel 220-*n* including an amplifier 221N that amplifies the reception signal, an analog-to-digital converter (ADC) 222N that converts the reception signal into a digital signal, and a signal processor 223N that receives the reception signal and acquires ultrasound image data on the basis of the reception signal.

In detail, the signal processor 223N may be implemented as a digital signal processor (DSP), and performs envelope detection for detecting magnitudes of ultrasound echo signals on the basis of the digital reception signal so that ultrasound image data is acquired.

The transmission channel 210-N may output a transmission signal for acquiring a frame of an ultrasound image. The transmission signal output by the transmission channel 210-N may correspond to an electrical signal. Frames of the ultrasound images may include an amplitude mode (A-mode) frame, a brightness mode (B-mode) frame, a color mode (C-mode) frame, a doppler mode (D-mode) frame, an elastography mode (E-mode) frame, a motion mode (M-mode) frame, and a frame of an elastography image.

In detail, the transmission channel 210-N may output a transmission signal according to a synchronization signal. The transmission channel 210-N may output a transmission signal with a time delay set on the basis of a synchronization signal having a pulse repetition frequency (PRF). Accordingly, the transmission signal may be a pulse having a repetition frequency.

In otherwords, although not shown in the drawing, the synchronization signal may be inputted to a beamformer and may be output with a predetermined time delay for each channel, and each signal output from the beamformer may be input to the pulsar included in the corresponding transmission channel 210-N, so that the transmission signal is output.

That is, the transmitter 210 including the plurality of transmission channels 210-1, 210-2, . . . , and 210-N may output a plurality of transmission signals. In detail, the transmitter 210 includes the plurality of transmission channels 210-1, 210-2, . . . , and 210-N each connected to a corresponding one of the plurality of transducer elements 121 of the ultrasound probe 120, and transmits a plurality of transmission signals to the plurality of transducer elements 121 through each of the transmission channels 210-1, 210-2, . . . , and 210-N.

The transmission signals generated and output by the transmission channels 210-1, 210-2, . . . , and 210-N may generally correspond to high voltage signals. In detail, the transmission signal may have a voltage of 200 Vp-p at the maximum. The reception signals output by the plurality of transducer elements 121 on the basis of the ultrasound echo signal reflected from the object correspond to low voltage signals compared to the transmission signals of the transmission channel. Therefore, the plurality of reception channels 220-1, 220-2, . . . , and 220-N of the ultrasound apparatus 100 may use a range corresponding to voltages of the reception signals of the plurality of transducer elements 121 as an input range.

The ultrasound probe 120 may be a part that comes into a contact with the body surface of the object or is inserted into the body of the object, and may transmit and receive ultrasound. In detail, the ultrasound probe 120, upon receiving a transmission signal transmitted from the transmitter 210, may convert the transmission signal into an ultrasound signal, transmit ultrasound into an object, receive an ultrasound echo signal reflected from a specific site inside the object, convert the ultrasound echo signal into a reception signal in the form of an electrical signal, and transmit the ultrasound echo signal to the receiver 220.

To this end, the ultrasound probe 120 may include the plurality of transducer elements 121 and a multiplexer (MUX) circuit. The plurality of transducer elements 121 may include a plurality of elements that may vibrate to convert an electrical signal into ultrasound or convert ultrasound into an electrical signal. The plurality of elements may be arranged on one surface of a housing of the ultrasound probe. In detail, the plurality of transducer elements 121 may be arranged in a direction parallel to an opening provided on the one surface of the housing such that ultrasound transmission and reception may be performed through the opening. The ultrasound probe 120 may convert a transmission signal into an ultrasound signal or convert an ultrasound echo signal into a reception signal using the plurality of transducer elements 121.

In detail, the plurality of transducer elements 121 may be implemented as piezoelectric transducers using piezoelectric effects. To this end, the transducer element 121 may include a piezoelectric material or a piezoelectric thin film. When alternating current is applied to the piezoelectric material or piezoelectric thin film from an internal charging device, such as a battery, or an external power supply device, the piezoelectric material or piezoelectric thin film vibrate with a predetermined frequency according to the applied alternating current and ultrasound waves of the predetermined frequency are generated according to the vibration frequency.

On the other hand, when ultrasound echo waves of the predetermined frequency reach the piezoelectric material or piezoelectric thin film, the piezoelectric material or piezoelectric thin film vibrates according to the ultrasound echo waves. In this regard, the piezoelectric material or piezoelectric thin film outputs alternating current of a frequency corresponding to the vibration frequency thereof.

In addition, the transducer element 121 may be implemented as other types of transducer elements, such as a magnetostrictive ultrasonic transducer using the magnetostrictive effect of a magnetic material, or a capacitive micromachining ultrasonic transducer (cMUT) that transmits and receives ultrasonic waves using vibrations of several hundreds or thousands of micromachined thin films.

Each of the plurality of transducer elements 121 of the ultrasound probe 120 is connected to a corresponding one of the transmission channels 210-1, 210-2, . . . , and 210-N of the plurality of channels to receive the transmission signal output by the transmitter 210. Each of the plurality of transducer elements 121 of the ultrasound probe 120 is also connected to a correspond one of the reception channels 220-1, 220-2, . . . , and 220-N included in the plurality of channels 200-1, 200-2, . . . and 200-N to transmit the reception signal to the signal processor of the corresponding one of the reception channels 220-1, 220-2, . . . and 220-N.

The reception channel 220-N may acquire ultrasound image data by receiving the reception signal that returns after the ultrasound signal has been transmitted to the object and reflected from the object. In detail, the reception channel 220-N may include an amplifier 221N for amplifying an input signal, an analog-to-digital converter (ADC) 222N for converting an input signal into a digital signal, and a signal processor 223N for acquiring ultrasound image data on the basis of a reception signal. That is, the reception channel 220-N may acquire the ultrasound image by amplifying the reception signal, converting the reception signal into a digital signal, and processing the digital signal.

As such, the reception channel 220-N in a single channel 200 acquires the ultrasound image data on the basis of the reception signal, and the ultrasound apparatus 100 including the channel in a plurality of units thereof (the total number of N) may acquire summed ultrasound image data by summing the pieces of ultrasound image data acquired through the plurality of channels 200-1, 200-2, . . . , and 200-N.

Accordingly, when a transmission channel 210-N included in the transmitter 210 has an error and the operation thereof is stopped, an ultrasound image acquired on the basis of the summed ultrasound image data may have a dark line defect as will be described below with reference to FIGS. 11A and 11B.

Referring to the drawings, the reception channel 220-N according to the embodiment of the present disclosure may generate and transmit a control signal for controlling the switching circuit 240-N, so that the switching circuit 240-N is controller.

In detail, the signal processor 223N of the reception channel 220-N may generate and transmit the control signal for controlling the switching circuit 240-N to control the switching circuit 240-N.

The ultrasound apparatus 100 according to the embodiment of the present disclosure may include the switching circuit 240-N including a switch 241-N for connecting the reception channel 220-N to the temperature detector 230-N that outputs the temperature information signal of the transmission channel 210-N and a resistance element 242-N.

The temperature detector 230-N may be a temperature sensor that detects heat of the transmission channel 210-N and outputs an electrical signal, and may be variously implemented without limitation as long as it can output a temperature information signal for detecting the temperature of the transmission channel 210-N.

The switching circuit 240-N may include the switch 241-N used to change opening/closing or a connection state of an electric circuit, and may include all components for closing or opening an electric circuit according to a control signal. For example, the switching circuit may be implemented as a metal oxide semiconductor field effect transistor (MOSFET).

The switch 241-N included in the switching circuit 240-N may be closed or opened on the basis of the control signal of the reception channel, and as will be described below, the switch 241-1 included in the switching circuit 240-N may be closed in a section other than a section in which the reception channel 220-N receives a reception signal and acquires ultrasound image data, on the basis of the control signal of the reception channel 220-N, so that a temperature information signal of the transmission channel 210-N is transmitted to the reception channel 220-N. In this case, the temperature information signal may be transmitted to the reception channel 220-N in the form of a voltage.

In addition, the switching circuit 240-N may include the resistance element 242-N, and a temperature information signal may be transmitted to the reception channel 220-N in the form of a current by the resistance element 242-N. In this case, since the temperature information signal of the transmission channel 210-N included in one channel 200 is transmitted to the reception channel 220-N in the form of a current, the resistance value of the resistance element 242-N may be set to be smaller than the resistance value of the resistance element 41 of the prior art for obtaining the temperature information signal of the transmitter 40 in the form of current. In addition, in a section other than a section in which a synchronization signal and a transmission signal are output, the switching circuit 240-N may be closed on the basis of a control signal of the reception channel 220-N such that temperature information of the transmission channel 210-N is transmitted to the reception channel 220-N.

In other words, the switching circuit 240-N, a simple configuration, is added such that the switching circuit 240-N is closed in a dummy section other than a section in which the reception channel 220-N of one channel 200 processes the reception signal, so that temperature information of the transmission channel 210-N for each channel is obtained with a simple circuit configuration without adding a separate configuration. In this case, even when the temperature information signal is an analog signal, the analog signal may be converted into a digital signal using the analog-to-digital converter 222N included in the conventional reception channel without using a separate analog-to-digital converter.

In addition, as will be described below, an error of the transmission channel 210-N for each channel may be detected through the temperature information, so that only the operation of the channel 200 having an error may be stopped and the ultrasound image data is corrected on the basis of a reception signal of a nearby channel, thereby preventing a dark line defect of the ultrasound image.

However, since the circuit of the reception channel 220-N may include a high pass filter, the sampling time of the control signal for closing the switching circuit 240-N may be provided to be short.

Hereinafter, a section for generating the control signal of the switching circuit 240-N according to the embodiment of the present disclosure will be described with reference to FIG. 6.

Figure 6:
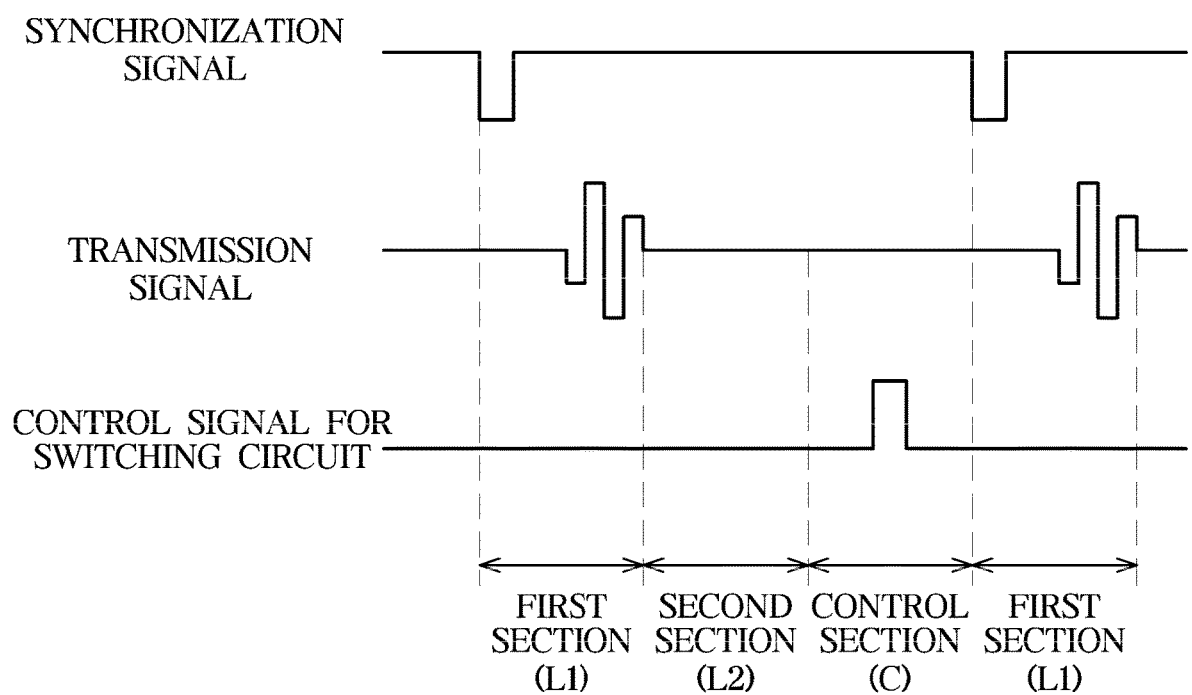
FIG. 6 is a diagram for describing a control section according to an embodiment.

FIG. 6 is a diagram for describing a control section according to an embodiment.

Referring to FIG. 6, a pulse power supply (not shown) included in the transmitter 210 may output a synchronization signal having a predetermined period. The beamformer may output a transmission signal for each transmission channel 210-N with a time delay set on the basis of the synchronization signal. Accordingly, the transmission signal may be a pulse having a constant period output from each transmission channel 210-N.

In a section in which the synchronization signal is output and the transmission signal is output on the basis of the synchronization signal (hereinafter, referred to as 'first section'; L1), the temperature detector 230-N has difficulty in transmitting a temperature information signal of the transmission channel 210-N because the synchronization signal is being output and the transmission signal is being generated and output on the basis of the synchronization signal. That is, when the reception channel 220-N allows the switching circuit 240-N to be closed in the first section L1, the reception channel 220-N may have difficulty in detecting an accurate temperature information signal.

Therefore, the signal processor 223N may generate a control signal for opening the switching circuit 240-N in the first section L1. In FIG. 6, the opening of the switching circuit 240-N is illustrated as being achieved by not generating any signal, but the control signal may vary according to the type of the switching circuit 240-N.

That is, in an implementation, the reception channel 220-N may generate a control signal for closing the switching circuit 240-N in a section other than the first section L1 such that the temperature information signal of the temperature detector 230-N is transmitted to the reception channel 220-N.

In a section in which the transducer element 121-N converts a transmission signal into an ultrasound signal, outputs the converted ultrasound signal, and transmits the converted ultrasound signal to an object, and the reception channel 220-N receive a reception signal that returns after the converted ultrasound signal has been transmitted to the object and reflected from the object, and the signal processor 223N acquires ultrasound image data (hereinafter, referred to as 'second section'; L2), even when the control signal for closing the switching circuit 240-N is generated, accurate temperature information may not be easily acquired because the signal processor 223N is processing the reception signal in the second section L2.

In other words, in the second section L2, the reception signal and the temperature information signal may overlap, and thus it may be difficult to detect the correct temperature information signal.

Therefore, the reception channel 220-N may generate a control signal for opening the switching circuit 240-N in the second section L2. In FIG. 6, the opening of the switching circuit 240-N is illustrated as being achieved by not generating any signal, but the control signal may vary according to the type of the switching circuit 240-N.

That is, in an implementation, the reception channel 220-N may generate a control signal for closing the switching circuit 240-N in a section other than the second section L2 such that the temperature information signal of the temperature detector 230-N through the temperature detector 230-N is transmitted to the reception channel 220-N.

In a section other than the first section L1 and the second section L2, it can be seen that the transmission channel 210-N and the reception channel 220-N do not output any signal or receive/process any signal. The section may be considered a dummy section, that is, a waste section, and may serve as a control section C in which the reception channel 220-N generates the control signal for closing the switching circuit 240-N.

As a result, when the reception channel 220-N generates the control signal for closing the switching circuit 240-N in the control period C, the temperature information signal of the transmission channel 210-N through the temperature detector 230-N may be transmitted to the reception channel 220-N through the closed switching circuit 240-N, and the reception channel 220-N may receive the temperature information signal.

In this case, the control signal generated by the reception channel 220-N may be a signal having a predetermined period for closing the switching circuit 240-N, and the predetermined period may be determined as a period D of the synchronization signal, or may be determined as a value obtained by multiplying the period D of the synchronization signal by a positive integer.

When the predetermined period of the control signal is the same as the period D of the synchronization signal, the temperature information signal of the transmission channel 210-N may be detected on a cycle in which ultrasound image data is acquired based on the synchronization signal, so that the reliability of the detected temperature information signal may be improved. However, since the failure of the transmission channel 210-N does not occur frequently, the period of the control signal may be appropriately determined by an integer multiple of the period D of the synchronization signal.

Hereinafter, an operation of the channel in a non-control section and a control section will be described with reference to FIGS. 7 to 8.

Figure 7:
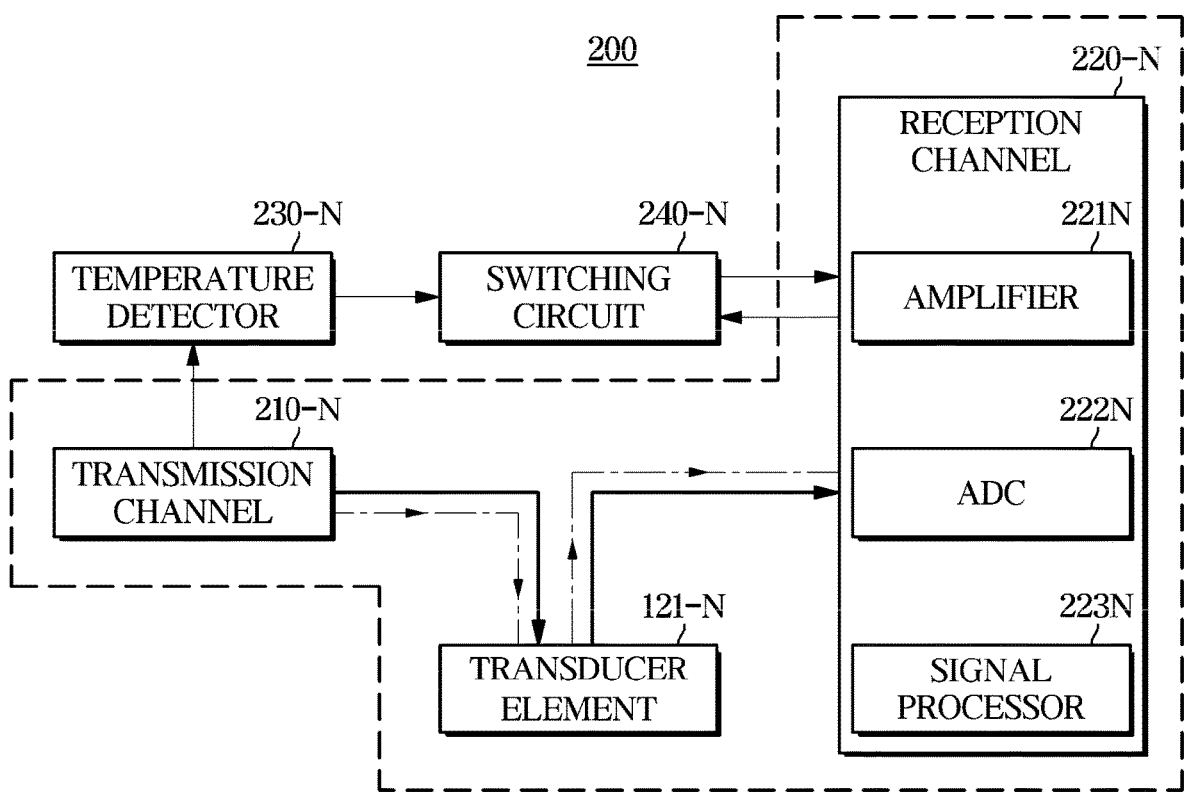
FIG. 7 is a diagram for describing a channel operation in a section other than a control section according to an embodiment.
Figure 8:
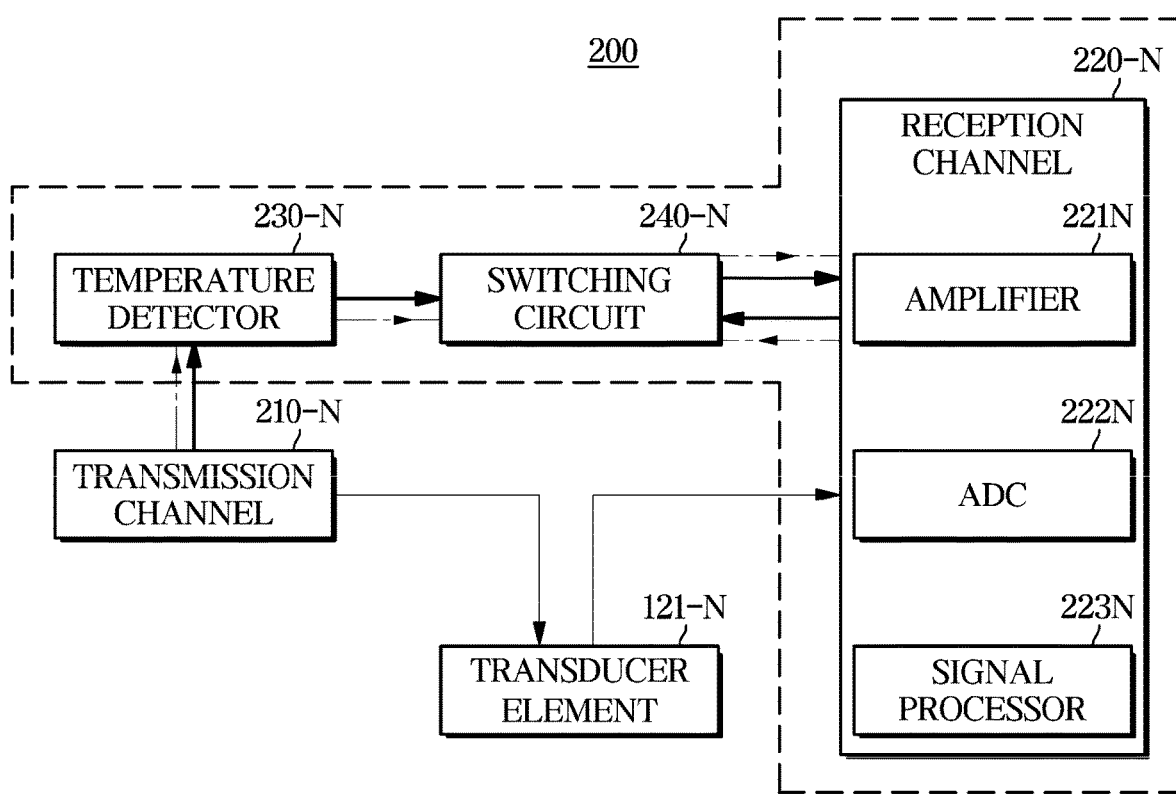
FIG. 8 is a diagram for describing a channel operation in a control section according to an embodiment.

FIG. 7 is a diagram for describing a channel operation in a section other than a control section according to an embodiment, and FIG. 8 is a diagram for describing a channel operation in a control section according to an embodiment.

Referring to FIG. 7, in a section other than the control section C, that is, in the first section L1 and the second section L2, the reception channel 220-N may generate a control for opening the switching circuit 240-N.

Since the switching circuit 240-N is opened, the temperature information signal of the transmission channel 210-N may not be transmitted to the reception channel 220-N through the temperature detector 230-N and the transmission channel 210-N may generate and output a transmission signal such that the transmission signal is input to the transducer element 121-N. The transduce element 121-N converts the transmission signal output from the transmission channel 210-N into an ultrasound signal and outputs the ultrasound signal, and a reception signal that returns after the ultrasound signal has been transmitted to an object and reflected from the object may be amplified by the amplifier 221N in the reception channel 220-N, and may be converted into a digital signal through the ADC 222N.

The reception channel 220-N may receive the amplified or digitally converted reception signal and transmit the received reception signal to the signal processor 223N. The signal processor 223N of the reception channel 220-N may acquire ultrasound image data on the basis of the reception signal, and when the ultrasound image is acquired, the first section L1 and the second section L2 may be terminated.

Referring to FIG. 8, in the control section C subsequent to the first section L1 and the second section L2, the signal processor 223N may generate a control signal for closing the switching circuit 240-N.

Upon being closed, the switching circuit 240-N may transmit a temperature information signal of the transmission channel to the reception channel 220-N through the temperature detector 230-N, and the temperature information signal may be amplified by the amplifier 221N or may be digitally converted through the ADC 222N in the reception channel 220-N. In the reception channel 220-N, the temperature information signal received after being amplified or digitally converted may be transmitted to the signal processor 223N, and the signal processor 223N may transmit the temperature information signal to the controller 150.

As described above with reference to FIGS. 4 to 8, the switching circuit 240-N is added to the conventional channel configuration, and the control signal for closing or opening the switching circuit 240-N in a predetermined section C is generated by the reception channel 220-N, so that the temperature information of the transmission channels 210-1, 210-2, . . . and 210-N for the respective channel 200-1, 200-2, . . . and 200-N of the transmitter 210 may be easily detected.

Hereinafter, the configuration of the ultrasound apparatus 100 including the plurality of channels 200 will be described.

Figure 9:
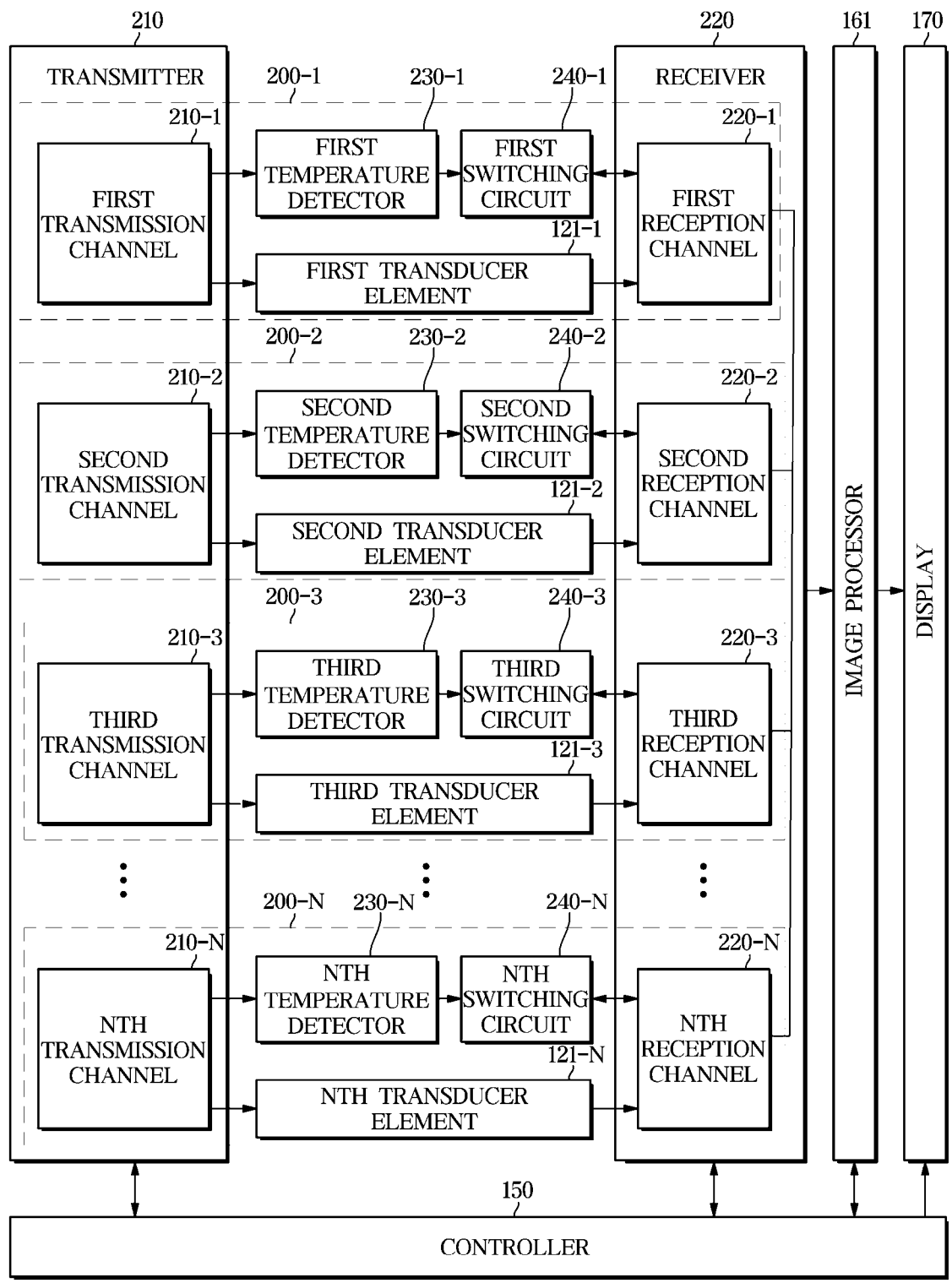
FIG. 9 is a block diagram illustrating an ultrasound apparatus including a plurality of channels according to an embodiment.

FIG. 9 is a block diagram illustrating the ultrasound apparatus including the plurality of channels according to the embodiment. Referring to FIG. 9, the plurality of channels 200-1, 200-2, . . . , and 200-N may be N channels (N is a natural number larger than or equal to 2). The ultrasound apparatus 100 according to the embodiment may include the transmitter 210 that generates and outputs a transmission signal, the plurality of switching circuits 240-1, 240-2, . . . and 240-N that connect temperature information signal of each transmission channel 210-1, 210-2, . . . , and 210-N of the transmitter 210 to the receiver 220, the plurality of transducer elements 121-1, 121-2, . . . , and 121-N each connected to a corresponding one of the transmission channel 210-1, 210-2, . . . and 210-N of the transmitter 210, and the receiver 220 that receives reception signals that return after ultrasound signals have been transmitted to an object and reflected from the object and acquires a plurality of pieces of ultrasound image data, the image processor 161 that sums the plurality of pieces of ultrasound image and performs various transformations and image processing such that the summed ultrasound image data is displayed on the display 170, the display 170 that displays various images, such as an ultrasound image, and the controller 150 that controls the transmitter 210, the receiver 210, the image processor 161, and the display 170.

The controller 150 may control the operation of the transmitter 210; determine whether the current section is the first section L1 or the second section L2 and control the receiver 220 to generate a control signal for closing or opening the switching circuits 240-1, 240-2, . . . and 240-n; and control the display 170 to display a phrase or a figure that indicates an error in the transmission channels 210-1, 210-2, . . . and 210-N.

Referring to FIG. 9, a process in which when one of the plurality of transmission channel 210-1, 210-2, . . . , and 210-N of the transmitter 210 has a temperature higher than or equal to a reference temperature, the operation of the corresponding one of the transmission channel 210-1, 210-2, . . . , and 210-N is stopped and ultrasound image data is acquired using a reception signal of a nearby channel is described.

The reference temperature may be determined in advance. For example, the reference temperature may be set to 100° C. such that when the temperature of the transmission channels 210-1, 210-2, . . . and 210-N is 100° C. or higher, it is determined that an error has occurred in the transmission channels 210-1, 210-2, . . . and 210-N, and the controller stops the operation of the transmission channels 210-1, 210-2, . . . and 210-N.

Hereinafter, for the sake of convenience in description, it may be assumed that the temperature of the second transmission channel 210-2 is higher than or equal to the reference temperature. The second reception channel 220-2 generates a control signal for closing the second switching circuit 240-2 in a control period C, and thus the second switching circuit 240-2 may be closed according to the control signal of the second reception channel 220-2. When the second switching circuit 240-2 is closed, a temperature information signal of the second transmission channel 210-2 may be transmitted to the second reception channel 220-2 through the second temperature detector 230-2.

The controller 150 may determine whether the temperature of the second transmission channel 210-2 is higher than or equal to the reference temperature on the basis of the temperature information signal received by the second reception channel 220-2, and in response to determining that the temperature is higher than or equal to the reference temperature, may stop the operation of the second transmission channel 210-2.

When the operation of the second transmission channel 210-2 is stopped, the second transmission channel 210-2 may not generate and output a transmission signal, and thus the second reception channel 220-2 may not receive any reception signal. Therefore, the second reception channel 220-2 may not acquire ultrasound image data based on the reception signal.

In this case, the second reception channel 220-2 may acquire ultrasound image data on the basis of a reception signal received by at least one of the first reception channel 220-1 or the third reception channel 220-3, which correspond to channels adjacent to the second reception channel 220-2, according to the control of the controller 150. For the sake of convenience in description, channels adjacent to the second channel 200-2 are assumed to be the first channel 200-1 and a third channel 200-3, but the channels adjacent to the second channel 200-2 may be more than or less than two channels. The number of the adjacent channels may vary depending on whether the plurality of transducer elements 121 of the ultrasound probe form a two-dimensional transducer array or a one-dimensional transducer array and may vary depending on the position of the transducer element 121-2 of the second channel 200-2 as will be described below with reference to FIG. 10.

In addition, the controller 150 may control the display 170 to indicate that the ultrasound apparatus 100 has an error when the temperature of the second transmission channel 210-2 is higher than or equal to the reference temperature. In addition, unlike the prior art, the controller 150 may control the display 170 to indicate that the channel 200-2 including the second transmission channel 210-2 has an error because the controller 150 is capable of determining whether the temperature of the second transmission channel 210-2 is higher than or equal to the reference temperature.

As such, according to the embodiment of the disclosure, when an error occurs in the second transmission channel 210-2, the second reception channel 220-2 may acquire ultrasound image data on the basis of at least one of the reception signal of the first reception channel 220-1 or the reception signal of the third reception channel 220-3 to prevent a dark line defect of an ultrasound image, and the display 170 may indicate that an error has occurred in the second transmission channel 210-2, thereby allowing the user to repair the second transmission channel 210-2.

Hereinafter, a channel adjacent to the second channel 200-2 among the plurality of channels 200-1, 200-2, . . . and 200-N is described.

Figure 10:
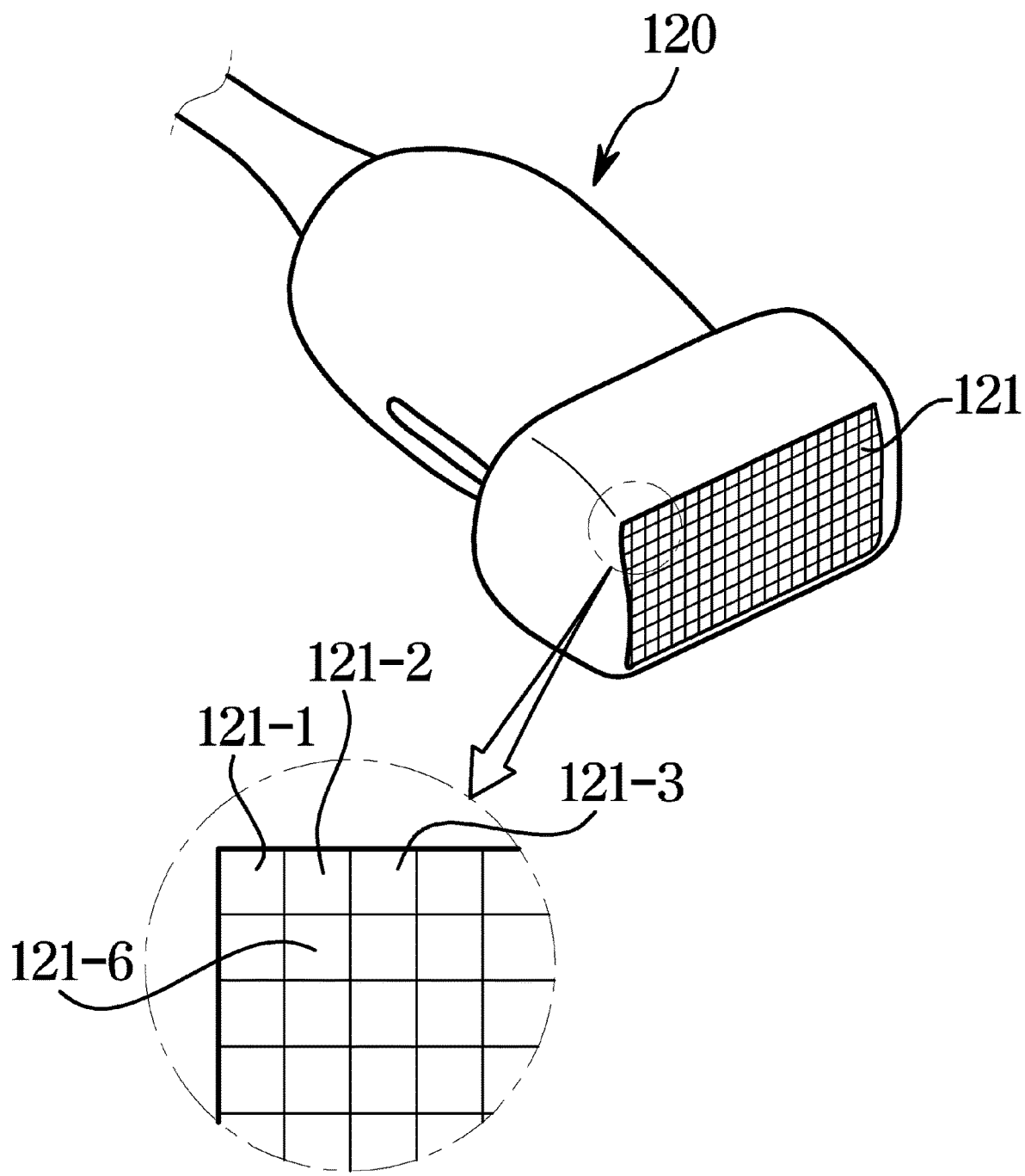
FIG. 10 is an external view illustrating an ultrasound probe including a two-dimensional array transducer according to an embodiment.

FIG. 10 is an external view illustrating the ultrasound probe including a two-dimensional array transducer according to an embodiment.

Referring to FIG. 10, the ultrasound probe 120 may include the plurality of transducer elements 121. The plurality of transducer elements 121 may be connected to the plurality of transmission channels 210-1, 210-2, . . . , and 210-N and the plurality of reception channels 220-1, 220-2, . . . , and 220-N, as described above. The plurality of transducer elements 121 may be implemented in a one-dimensional array, and arranged in a linear form or in a convex form. In both cases, the basic operation principle of the ultrasound probe is the same, but in the case of the convex type probe, since the ultrasound signals are radiated from the plurality of transducer elements 121 in a fan-shape, the generated ultrasound image may also have a fan-shape.

The plurality of transducer elements 121 may be implemented in a two-dimensional array, as shown in FIG. 10. In this case, the second transducer element 121-2 connected to the second transmission channel 210-2 may be arranged as shown in FIG. 10, and transducer elements adjacent to the second transducer element 121-2 may include the first transducer element 121-1, the third transducer element 121-3, and the sixth transducer element 121-6.

In other words, in the plurality of channels 200-1, 200-2, . . . and, 200-N, channels adjacent to a specific channel 200-2 may be one or more channels 200-1, 200-3, and 200-6 including the transducer elements 121-1, 121-3, and 121-6 adjacent to the transducer element 121-2 of the specific channel 200-2. That is, when the transducer elements 121 are adjacent to each other, the positional difference of ultrasound signals transmitted from the transducer elements 121 to an object is small, and thus reception signals received by the reception channels 220-1, 220-2, 220-3, and 220-6 merely have a small difference from each other. Accordingly, when an error occurs in a specific transmission channel 210-2, in order to correct a dark line defect in the ultrasound image caused by the stopped operation of the transmission channel 210-2, ultrasound image data is acquired on the basis of the reception signals of the adjacent channels 200-1, 200-3, and 200-6.

Hereinafter, referring to FIGS. 11A to 11B, an ultrasound image corrected with regard to a dark line defect according to an embodiment of the present disclosure is described.

Figure 11A:
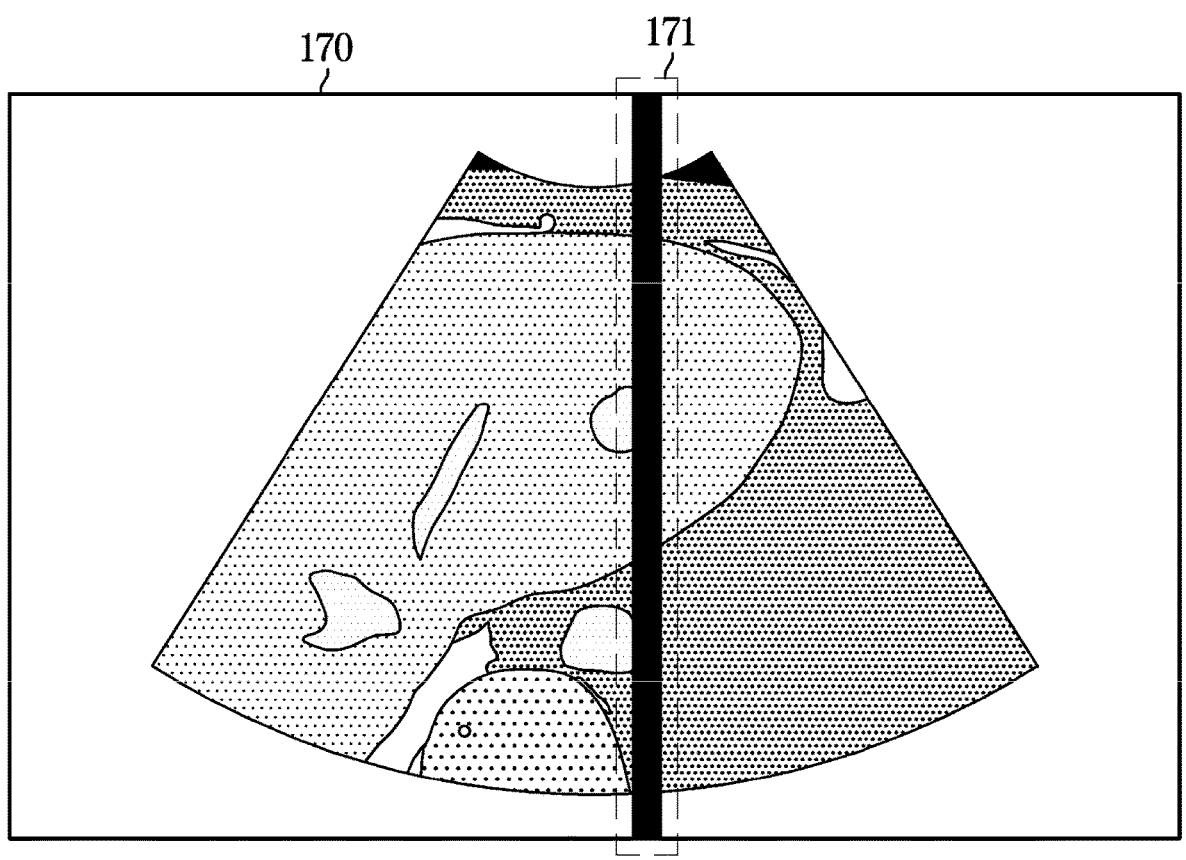
FIG. 11A is a diagram for describing an image correction process of an ultrasound apparatus according to an embodiment.

FIGS. 11A to 10B are diagrams for describing an image correction process of the ultrasound apparatus according to the embodiment. Referring to FIG. 11A, when an error occurs in a specific transmission channel (one of the transmission channels 210-1, 210-2, . . . , and 210-N of the transmitter 210, e.g., the second transmission channel 210-2), the transmission channel 210-2 is broken, and thus the reception channel 220-2 corresponding to the broken transmission channel 210-2 may not receive a reception signal and may not acquire ultrasound image data.

According to the embodiment of the present disclosure, when an error occurs in the specific transmission channel 210-2 of the transmitter 210, the controller 150 stops the operation of the transmission channel 210-2 before the transmission channel 210-2 is broken. Accordingly, the reception channel 220-2 corresponding to the transmission channel 210-2 may not receive a reception signal and thus fail to acquire ultrasound image data.

Since the reception channel 220-2 of the channel 200-2 including the erroneous transmission channel 210-2 fails to acquire ultrasound image data, a dark line defect may occur in an ultrasound image portion 171 corresponding to the erroneous reception channel 220-2. The dark line defect may refer to a phenomenon in which no image is output in the ultrasound image portion 171 corresponding to the reception channel 220-2 because the reception channel 220-2 does not output any data.

When such a dark line defect occurs, the user may have difficulty in checking the ultrasound image, and the reliability of the ultrasound apparatus 100 may be reduced.

Figure 11B:
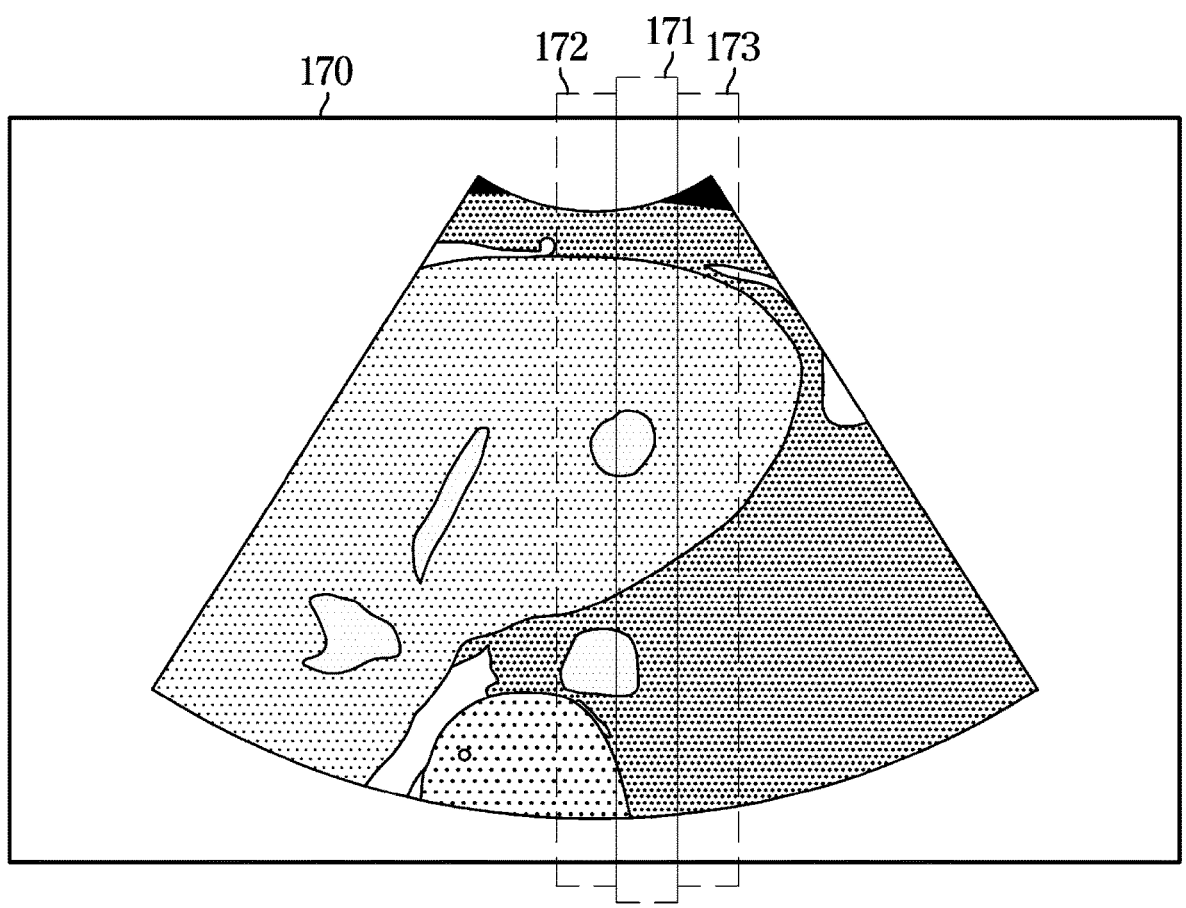
FIG. 11B is a diagram for describing an image correction process of an ultrasound apparatus according to an embodiment.

Referring to FIG. 11B, it can be seen that an image of an ultrasound image is corrected according to an embodiment of the present disclosure.

That is, the reception channel 220-2 corresponding to the transmission channel 210-2 in which the operation is stopped acquires ultrasound image data on the basis of reception signals received by the reception channels 220-1, 220-3, and 220-6 of the nearby channels 200-1, 200-3, and 200-6 according to control of the controller 150, and thus a dark line defect may be prevented.

For example, the acquiring of the ultrasound image data by the reception channel 220-2 of the erroneous channel 200-2 on the basis of reception signals received by the reception channels 220-1, 220-3, and 220-6 of the nearby channels 200-1, 200-3, and 200-6 includes calculating an average value of the reception signals of the reception channels 220-1, 220-3 and 220-6 included in the nearby channels 200-1, 200-3 and 200-6 and acquiring the calculated average value as the ultrasound image data.

That is, the ultrasound image portion 171 corresponding to the erroneous reception channel 220-2 may be corrected on the basis of an ultrasound image portion 172 corresponding to the reception channel 220-1 of a nearby channel 200-1 or an ultrasound image portion 173 corresponding to the reception channel 220-3 of another nearby channel 200-3.

Figure 12:
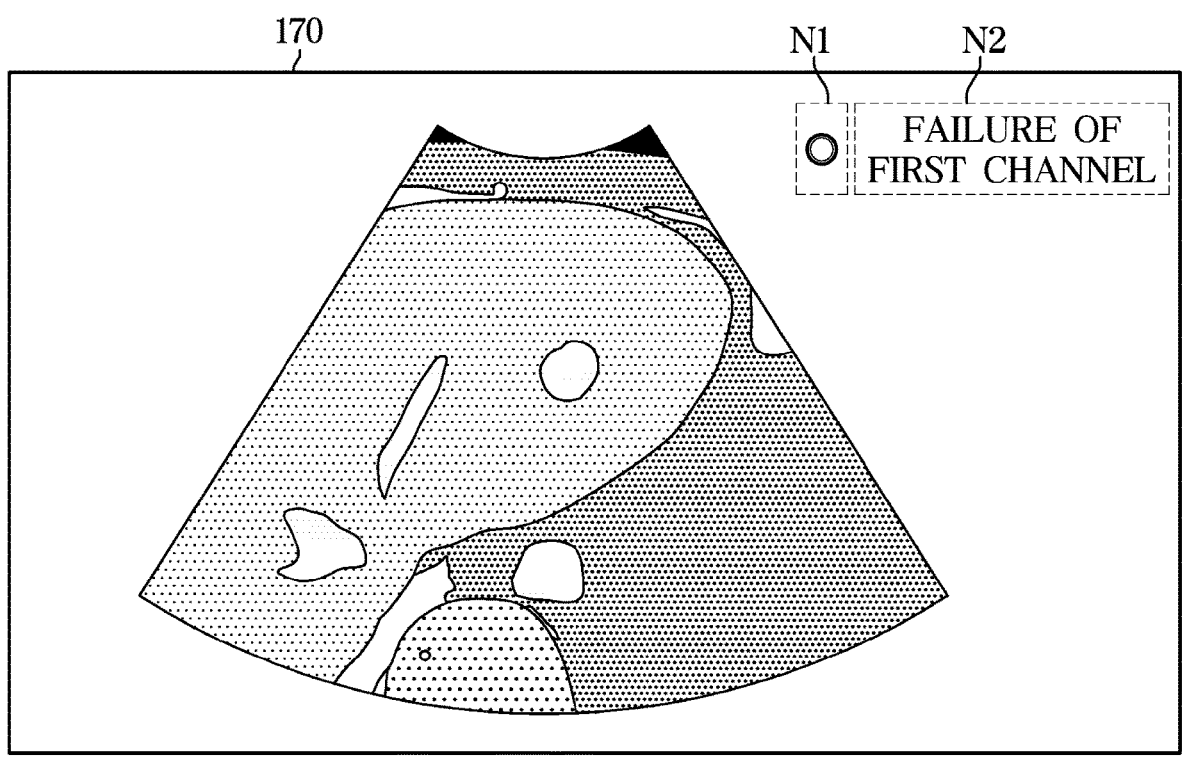
FIG. 12 is a diagram illustrating an image displayed on a display when an error of a transmission channel is detected according to an embodiment.

FIG. 12 is a diagram illustrating an image displayed on a display when an error of a transmission channel is detected according to an embodiment. For the sake of convenience in description, it is assumed that the temperature of the transmission channel 210-1 of the first channel 200-1 is higher than or equal to the reference temperature.

Referring to FIG. 12, when the temperature of the transmission channel 210-1 of the transmitter 210 is higher than or equal to the reference temperature, the controller 150 controls the display 170 to indicate that an error exists in the ultrasound apparatus 100. In addition, the controller 150 may control the display 170 to indicate that an error exists in the channel 200-1 including the transmission channel 210-1 having a temperature higher than or equal to the reference temperature.

The display 170 may display a phrase (N2), a figure (N1), and the like to notify the user that an error exists in the channel including the erroneous transmission channel under the control of the controller 150.

For example, as illustrated in the drawing, the display 170 may display a figure N1 indicating that an error exists in the ultrasound apparatus 100, and a phrase N2 indicating that an error exists in the channel 200-1 including the erroneous transmission channel 210-1. The figure N1 or the phrase N2 may be a predetermined figure or phrase.

Hereinafter, a method of controlling the ultrasound apparatus 100 according to an embodiment of the present disclosure will be described with reference to FIG. 13.

Figure 13:
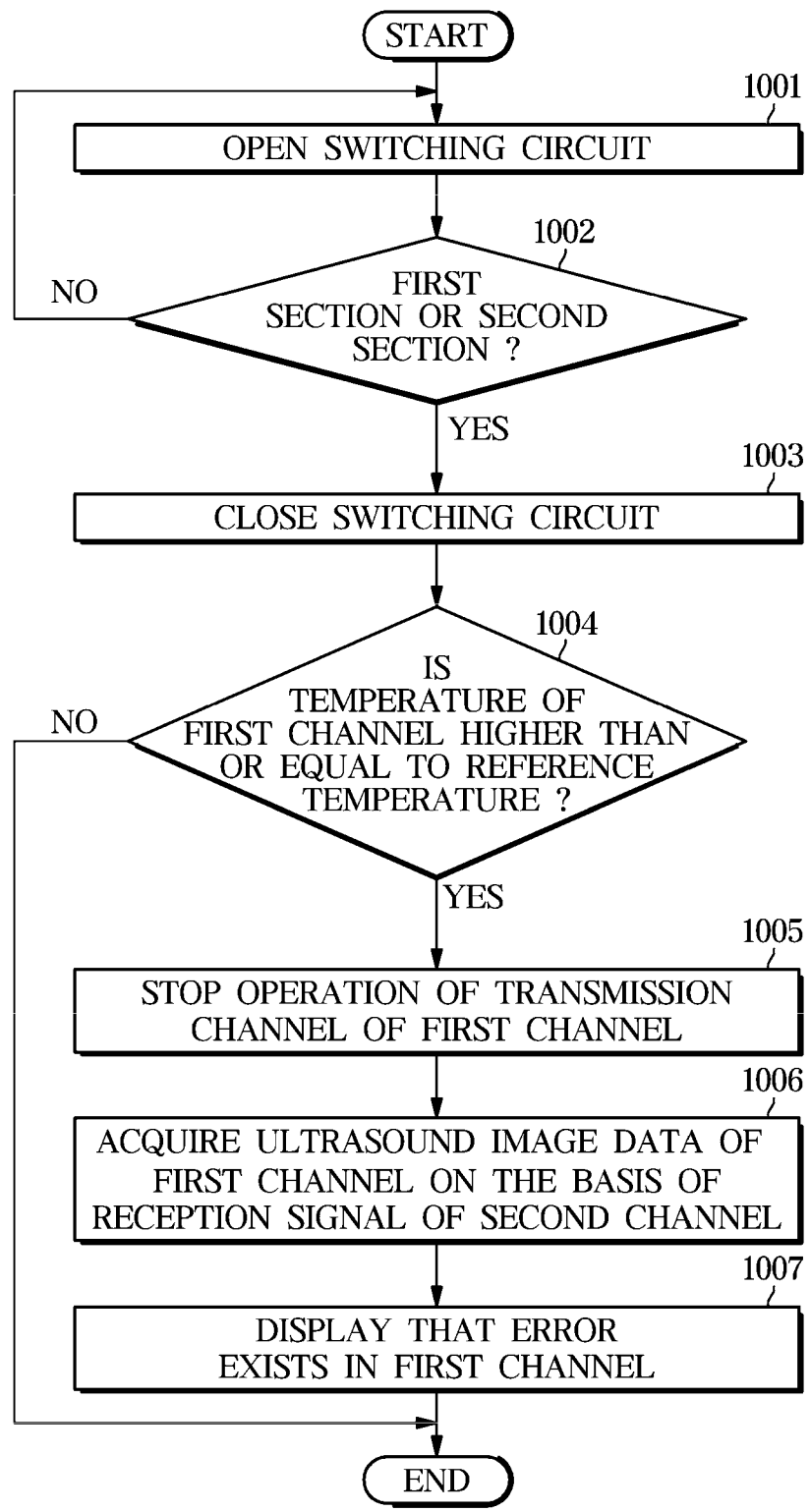
FIG. 13 is a flowchart showing a method of controlling an ultrasound apparatus according to an embodiment.

FIG. 13 is a flowchart showing a method of controlling an ultrasound apparatus according to an embodiment. Referring to FIG. 13, the method of controlling the ultrasound apparatus 100 according to the embodiment may start with the switching circuits 240-1, 240-2, . . . , and 240-N opened (1001).

As described above, when the current section is the first section L1 in which the synchronization signal or the transmission signal are output or the second section L2 in which the reception channels 220-1, 220-2, . . . , and 220-N acquire ultrasound image data on the basis of reception signals, the reception channels 220-1, 220-2, . . . and, 220-N generate a control signal for opening the switching circuits 240-1, 240-2, . . . , and 240-N to keep the switching circuits 240-1, 240-2, . . . , and 240-N open (1002).

When the current section is not the first section L1 or the second section L2, the reception channels 220-1, 220-2, . . . and 220-N may generate a control signal for closing the switching circuits 240-1, 240-2, . . . and 240-N (1003). In this case, the switching circuits 240-1, 240-2, . . . and, 240-N may be closed on the basis of the control signals of the reception channels 220-1, 220-2, . . . and 210-N, and temperature information signals of the transmission channels 210-1, 210-2, . . . and 210-N may be transmitted to the reception channels 220-1, 220-2, . . . , and 220-N.

The controller 150 may determine whether the temperature of the transmission channel 210-1 included in a channel (one of the channels 200-1, 200-2, . . . , and 200-N, for example, the first channel 200-1) is higher than or equal to the reference temperature on the basis of the temperature information signals received by the reception channels 220-1, 220-2, . . . , and 220-N (1004), and in response to determining that the temperature of the transmission channel 210-1 included in the first channel 200-1 is not higher than or equal to the reference temperature, terminates the procedure, and in response to determining that the temperature of the transmission channel 210-1 included in the first channel 200-1 is higher than or equal to the reference temperature, stop the operation of the transmission channel 210-1 of the first channel 200-1 (1005).

The controller 150 may control the reception channel 220-1 of the first channel 200-1 to acquire the ultrasound image data on the basis of the reception signal received by the reception channel 200-2 of the channel (one or more of the channels 200-2, 200-3, . . . and 200-N, for example, the second channel 200-2), so that the ultrasound image data of the first channel 200-1 may be acquired (1006).

As described above, the second channel 200-2 may be determined as a channel including the transducer element 121-2 adjacent to the transducer element 121-1 of the first channel 200-1.

In addition, the controller 150 may display that an error exists in the first channel 200-1 (1007), and may also display that an error exists in the ultrasound apparatus 100.

As is apparent from the above, the ultrasound apparatus and the method of controlling the same can individually detect temperature information of a plurality of transmission circuits by only adding a simple circuit configuration, so that image defect due to damage of the transmission circuit is corrected while preventing a series of damage of nearby circuits.

What is claimed is:

1. An ultrasound apparatus including a plurality of channels, each comprising:
   a transmission channel configured to generate and output a transmission signal on the basis of a synchronization signal;
   a temperature detector configured to output a temperature information signal of the transmission channel;
   a transducer element configured to convert the transmission signal output from the transmission channel into an ultrasound signal and output the ultrasound signal;
   a reception channel configured to receive a reception signal that returns after the ultrasound signal is transmitted to an object and is reflected from the object, and acquire ultrasound image data on the basis of the received reception signal; and
   a switching circuit configured to connect the temperature detector to the reception channel such that the reception channel receives the temperature information signal of the transmission channel,
   wherein the reception channel is configured to generate a control signal for closing or opening the switching circuit,
   the switching circuit is closed or opened based on the generated control signal,
   wherein the reception channel is configured to generate the control signal for closing the switching circuit in a dummy section other than a first section and a second section such that the temperature information signal of the transmission channel is transmitted to the reception channel,
   the first section is a section in which the synchronization signal and the transmission signal are output, and
   the second section is a section in which the reception channel acquires the ultrasound image data on the basis of the reception signal.

2. The ultrasound apparatus of claim 1, wherein the reception channel generates the control signal for opening the switching circuit in the first section such that the output temperature information signal is prevented from being transmitted to the reception channel.

3. The ultrasound apparatus of claim 1, wherein the reception channel generates the control signal for opening the switching circuit in the second section such that the output temperature information signal is prevented from being transmitted to the reception channel.

4. The ultrasound apparatus of claim 1, further comprising a controller configured to control an operation of the transmission channel,
   wherein the controller determines whether a temperature of the transmission channel is higher than or equal to a reference temperature on the basis of the temperature information signal received by the reception channel, and in response to the temperature of the transmission channel being higher than or equal to the reference temperature, stops operating the transmission channel.

5. The ultrasound apparatus of claim 4, wherein the plurality of channels includes a first channel and a second channel including a transducer element adjacent to a transducer element of the first channel,
   wherein the controller, in response to a temperature of the transmission channel included in the first channel being higher than or equal to the reference temperature, stops operating the transmission channel included in the first channel, and controls the reception channel of the first channel such that the reception channel of the first channel acquires the ultrasound image data on the basis of a reception signal received by the reception channel of the second channel.

6. The ultrasound apparatus of claim 4, further comprising a display, wherein the controller, in response to the temperature of the transmission channel being higher than or equal to the reference temperature, allows the display to indicate that an error exists in the ultrasound apparatus.

7. The ultrasound apparatus of claim 4, further comprising a display, wherein the controller, in response to the temperature of the transmission channel being higher than or equal to the reference temperature, allows the display to indicate that an error exists in the channel including the transmission channel.

8. The ultrasound apparatus of claim 1, wherein the reception channel is configured to generate the control signal having a predetermined period, and
   the predetermined period is a value obtained by multiplying a period of the synchronization signal by a positive integer.

9. A method of controlling an ultrasound apparatus including a plurality of channels each including a transmission channel, a temperature detector, a transducer element, a reception channel, and a switching circuit configured to connect the temperature detector and the reception channel, the method comprising:
   generating and outputting a transmission signal on the basis of a synchronization signal;
   converting the output transmission signal into an ultrasound signal and output the ultrasound signal;
   receiving a reception signal that returns after the ultrasound signal is transmitted to an object and is reflected from the object, and acquiring ultrasound image data on the basis of the received reception signal;
   outputting a temperature information signal of the transmission channel; and
   generating a control signal for closing or opening the switching circuit such that the reception channel receives the output temperature information signal of the transmission channel,
   wherein the generating of the control signal for closing the switching circuit includes generating the control signal for closing the switching circuit in a dummy section other than a first section and a second section such that the temperature information signal of the transmission channel is transmitted to the reception channel, the first section is a section in which the synchronization signal and the transmission signal are output, and
   the second section is a section in which the reception channel acquires the ultrasound image data on the basis of the reception signal.

10. The method of claim 9, further comprising generating the control signal for opening the switching circuit in the first section such that the output temperature information signal is prevented from being transmitted to the reception channel.

11. The method of claim 9, further comprising generating the control signal for opening the switching circuit in the second section such that the output temperature information signal is prevented from being transmitted to the reception channel.

12. The method of claim 9, further comprising determining whether a temperature of the transmission channel is higher than or equal to a reference temperature on the basis of the temperature information signal received by the reception channel, and in response to the temperature of the transmission channel being higher than or equal to the reference temperature, stopping the operation of the transmission channel.

13. The method of claim 12, wherein the plurality of channels includes a first channel and a second channel including a transducer element adjacent to a transducer element of the first channel, further comprising, in response to a temperature of the transmission channel included in the first channel being higher than or equal to the reference temperature, stopping the operation of the transmission channel included in the first channel, and controlling the reception channel of the first channel such that the reception channel of the first channel acquires the ultrasound image data on the basis of a reception signal received by the reception channel of the second channel.

14. The method of claim 12, further comprising:
in response to the temperature of the transmission channel being higher than or equal to the reference temperature, indicating an error exists in the ultrasound apparatus.

15. The method of claim 12, further comprising:
in response to the temperature of the transmission channel being higher than or equal to the reference temperature, indicating an error exists in the channel including the transmission channel.

16. The method of claim 9, wherein the generating of the control signal for closing or opening the switching circuit includes generating the control signal having a predetermined period, and
the predetermined period is a value obtained by multiplying a period of the synchronization signal by a positive integer.

\* \* \* \* \*